United States Patent
Berghash

(10) Patent No.: US 6,280,196 B1
(45) Date of Patent: Aug. 28, 2001

(54) DISPOSABLE TOOTH BLEACHING TRAY

(75) Inventor: Robert D. Berghash, Williamsville, NY (US)

(73) Assignee: Shield Mfg. Inc., Tonawanda, NY (US)

( * ) Notice: Subject to any disclaimer, the term of this patent is extended or adjusted under 35 U.S.C. 154(b) by 0 days.

(21) Appl. No.: 09/690,086

(22) Filed: Oct. 16, 2000

(51) Int. Cl.$^7$ ...................................................... A61C 5/00

(52) U.S. Cl. .............................................. 433/215; 433/37

(58) Field of Search ...................................... 433/215, 214, 433/37, 38, 34, 41, 80; 128/861, 862

(56) References Cited

U.S. PATENT DOCUMENTS

| | | | |
|---|---|---|---|
| 4,138,814 | * | 2/1979 | Weltzman ............................ 433/215 |
| 5,460,527 | * | 10/1995 | Kittelsen ............................. 433/215 |
| 6,017,217 | * | 1/2000 | Wittrock ................................ 433/37 |
| 6,132,208 | * | 10/2000 | Mathieu .................................. 433/6 |

* cited by examiner

Primary Examiner—John J. Wilson
Assistant Examiner—Melba Bumgarner
(74) Attorney, Agent, or Firm—Phillips, Lytle, Hitchcock, Blaine & Huber LLP

(57) ABSTRACT

A tooth bleaching tray (20) broadly includes a U-shaped trough-like member (21) having a central arcuate portion (22) and having an extension portion (23, 24) continuing from either end thereof and terminating in a distal end (25, 26). The tray has an outer wall (28) adapted to face toward the outer surface of a person's teeth, an inner wall (29) adapted to face toward the inner surface of such person's teeth, and a bottom surface (30) joining the lower margins of the inner and outer walls. A thin flexible wall (31, 32) is located at each extension portion distal end (25, 26) and joins the margins of the inner and outer walls and the bottom surface. This flexible portion is adapted to conform to the shape of such person's rearwardmost molar without deformation of the trough-like member, and functions as a dam to prevent bleaching composition from flowing out of the trough-like member through the distal ends.

8 Claims, 1 Drawing Sheet

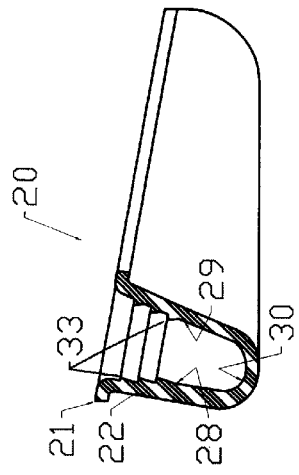
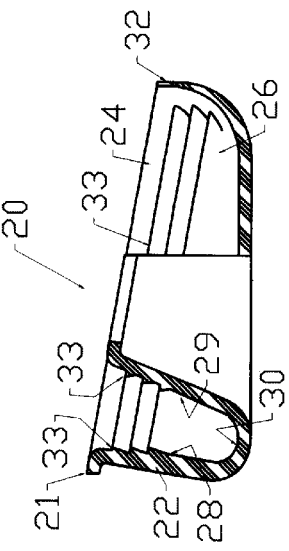
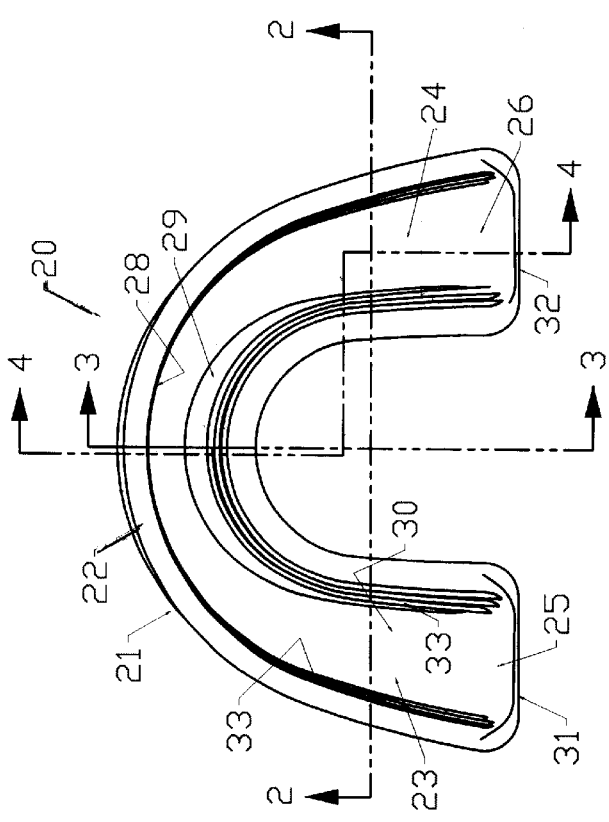
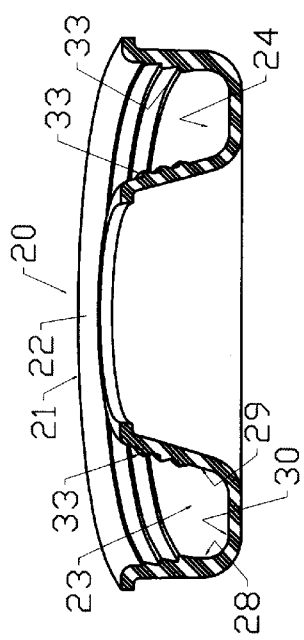

DISPOSABLE TOOTH BLEACHING TRAY

TECHNICAL FIELD

The present invention relates generally to an improved tooth bleaching tray, and, more particularly, to a disposable tooth bleaching tray having means for retaining the bleaching composition in a trough-like member and for reducing the possibility of such bleaching composition contacting a person's gums.

BACKGROUND ART

In recent years, it has become fashionable to periodically bleach one's teeth in order to accentuate their whiteness. There are various known bleaching compositions that are used for this purpose. In general, the prior art has contemplated the U-shaped trough-like member to hold the bleaching composition in contact with the person's teeth while being bleached.

However, in some cases, the bleaching composition will run out of the rear of the trough-like member, or be displaced upwardly so as to contact a person's gums. In general, it would desirable to retain the bleaching composition in the trough so as to contact a person's teeth, and to prevent such composition from unduly contacting the person's gums.

DISCLOSURE OF THE INVENTION

With parenthetical reference to the corresponding parts, portions or surfaces of the disclosed embodiment, merely for purposes of illustration and not by way of limitation, the present invention broadly provides an improved tooth bleaching tray (20).

The improved tray broadly includes a U-shaped trough-like member (21) having a central arcuate portion (22) and having an extension portion (23, 24) continuing from either end thereof and terminating in a distal end (25, 26). The tray has an outer wall (28) adapted to face toward the outer surface of a person's teeth, an inner wall (29) adapted to face toward the inner surface of such person's teeth, and a bottom surface (30) joining the lower margins of the inner and outer walls. A thin flexible wall (31, 32) is located at each extension portion distal end andjoining the margins of said inner and outer walls and said bottom. Each flexible portion being adapted to conform to the shape of such person's rearwardmost molar without deformation of said trough-like member and functions as a dam to prevent the bleaching composition from flowing out of the trough-like member through the distal ends.

In the preferred embodiment, the bottom surface is generally arcuate between the inner and outer walls in the vicinity of arcuate portion 22, but is generally flat or planar toward the distal ends ofthe extensions. The inner and outer walls are preferably inclined in the vicinity of the arcuate portion to conform to the normal inclination of a person's teeth. This angle of inclination may be about 9°.

In the preferred embodiment, a plurality of ribs are provided on the inner surface to reduce the possibility of the bleaching composition contacting the person's gums.

Accordingly, the general object of the invention is to provide an improved tooth bleaching tray.

Another object is to provide an improved disposable tooth bleaching tray having flexible end walls that are adapted to retain bleaching composition in the trough-like member.

Another object is to provide an improved tooth bleaching tray having a plurality of ribs to minimize the possibility of the bleaching composition contacting a person's gums.

These and other objects and advantages will become apparent from the foregoing and ongoing written specification, the drawings, and the appended claims.

BRIEF DESCRIPTION OF THE DRAWINGS

FIG. 1 is a top plan view of the improved tooth bleaching tray.

FIG. 2 is a fragmentary vertical sectional view thereof, taken generally on line 2—2 of FIG. 1.

FIG. 3 is a fragmentary vertical sectional view thereof, taken generally on line 3—3 of FIG. 1.

FIG. 4 is a fragmentary vertical sectional view thereof, taken generally on line 4—4 of FIG. 1.

DESCRIPTION OF THE PREFERRED EMBODIMENT

At the outset, it should be clearly understood that like reference numerals are intended to identify the same structural elements, portions or surfaces consistently throughout the several drawing figures, as such elements, portions or surfaces may be further described or explained by the entire written specification of which this detailed description is an integral part. Unless otherwise indicated, the drawings are intended to be read (e.g., cross-hatching, arrangement of parts, proportion, degree, etc.) together with the specification, and are to be considered a portion of the entire written description of this invention. As used in the following description, the terms "horizontal", "vertical", "left", "right", "up" and "down", as well as adjectival and adverbial derivatives thereof (e.g., "horizontally", "rightwardly", "upwardly", etc.), simply refer to the orientation of the illustrated structure as the particular drawing figure faces the reader. Similarly, the terms "inwardly" and "outwardly" generally refer to the orientation of a surface relative to its axis of elongation, or axis of rotation, as appropriate.

Referring now to the drawings, and, more particularly, to FIG. 1 thereof, the improved tooth bleaching tray is generally indicated at 20. Tray 20 is shown in top plan as including a generally inverted U-shaped trough-like member 21 having a central arcuate portion 22 and having lateral extension portions 23, 24 continuing downwardly from either end thereof. These two extension portions are shown as terminating in distal ends 25, 26, respectively.

The tray is shown as having an outer wall 28 that is adapted to face toward the outer surface of a person's teeth (not shown), an inner wall 29 that is adapted to face toward the inner surface of a person's teeth, and a bottom surface 30. As best shown in FIGS. 2–4, this bottom surface is generally arcuate between the inner and outer walls in the vicinity of arcuate portion 22 and is generally flat or planar in the vicinity of the distal ends of the extensions.

Adverting now to FIG. 1, thin flexible portions 31,32 are located the extension portion distal ends 25, 26, respectively. These flexible walls join the inner and outer walls and the bottom. The flexible portions are adapted to conform to the shape of a person's rearward-most molar without deformation of the trough-like member, and function as a dam to prevent the bleaching composition (not shown) from flowing out of the trough-like member through the distal ends when a person's teeth are submerged therein.

The inner and outer walls are inclined in the vicinity ofthe arcuate portion to conform to the normal inclination of a person's teeth. In the accompanying drawings, the arcuate portion inner and outer walls as shown as being inclined by an angle of about 9° with respect to the vertical.

In addition to the foregoing, a plurality of ribs, severally indicated at 33, are provided on the inner and outer walls along substantially the entire length of the U-shaped surfaces thereof. These ribs are adapted to engage a person's gums so as to prevent the bleaching composition from splashing into engagement therewith. The improved tray should be flexible, and desirably made of a closed self-foam or a flexible thermoplastic. The thickness of the tray varies from about 0.030–0.080 inches at different points, with the flexible portion being on the order of 0.010–0.020 inches in thickness. The number, size and shapes of the ribs can readily be varied, as desired.

Therefore, while the presently-preferred form of the improved tooth bleaching tray as been shown and described, and several modifications thereof discussed, persons skilled in this art will readily appreciate that various additional changes and modifications may be made without departing from the spirit of the invention, as defined and differentiated by the following claims.

What is claimed is:

1. A tooth bleaching tray, comprising:

a U-shaped trough-like member having a central arcuate portion and having an extension portion continuing from either end thereof and terminating in a distal end;

said tray having an outer wall adapted to face toward the outer surface of a person's teeth, having an inner wall adapted to face toward the inner surface of said person's teeth, and having a bottom surface joining the lower margins of said inner and outer walls; and a thin flexible portion located at each extension portion distal end and joining the margins of said inner and outer walls and said bottom surface, said flexible portion being adapted to conform to the shape of said person's rearwardmost molar without deformation of said trough-like member and functioning as a dam to prevent a bleaching composition from flowing out of said trough-like member through said distal ends.

2. A tooth bleaching tray as set forth in claim 1 wherein said bottom surface is arcuate between said inner and outer walls.

3. A tooth bleaching tray as set forth in claim 1 wherein said inner and outer walls are inclined in the vicinity of said arcuate portion to conform to the normal inclination of said person's teeth.

4. A tooth bleaching tray as set forth in claim 1 wherein said inner and outer walls are inclined at an angle of about 9°.

5. A tooth bleaching tray as set forth in claim 1 and further comprising at least one rib on said inner surface to reduce the possibility of said bleaching composition engaging said person's gum.

6. A tooth bleaching tray as set forth in claim 5 and further comprising a plurality of said ribs on said inner surface.

7. A tooth bleaching tray as set forth in claim 1 and further comprising at least one rib on said outer surface to reduce the possibility of said bleaching composition engaging said person's gum.

8. A tooth bleaching tray as set forth in claim 7 and further comprising a plurality of said ribs on said outer surface.

* * * * *